(12) United States Patent
Jemsby et al.

(10) Patent No.: US 8,388,248 B2
(45) Date of Patent: Mar. 5, 2013

(54) MEDICAL LIQUID APPLICATOR SYSTEM

(75) Inventors: Bjoern N. (Niklas) Jemsby, Atlanta, GA (US); Tore G. Wistedt, Marietta, GA (US); Ajay Y. Houde, Duluth, GA (US); Joseph A. Cesa, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 921 days.

(21) Appl. No.: 12/345,961

(22) Filed: Dec. 30, 2008

(65) Prior Publication Data

US 2010/0166485 A1 Jul. 1, 2010

(51) Int. Cl.
*B43K 5/14* (2006.01)
(52) U.S. Cl. ........................................................ 401/132
(58) Field of Classification Search ........... 401/132–135
See application file for complete search history.

(56) References Cited

U.S. PATENT DOCUMENTS

| | | | |
|---|---|---|---|
| 3,048,878 A | 8/1962 | Gray et al. |
| 3,315,801 A | 4/1967 | Lowry |
| 3,369,267 A | 2/1968 | Friedland et al. |
| 3,418,059 A | 12/1968 | Robe |
| 3,521,805 A | 7/1970 | Ward |
| 3,826,259 A | 7/1974 | Bailey |
| 3,917,116 A | 11/1975 | Mason |
| 3,986,640 A | 10/1976 | Redmond |
| 4,084,910 A | 4/1978 | Larosa |
| 4,140,409 A | 2/1979 | Devries |
| 4,173,978 A | 11/1979 | Brown |
| 4,236,652 A | 12/1980 | Beguhn |
| 4,430,013 A | 2/1984 | Kaufman |
| 4,493,574 A | 1/1985 | Redmond et al. |
| 4,611,715 A | 9/1986 | Redmond |
| 4,668,557 A | 5/1987 | Lakes |

(Continued)

FOREIGN PATENT DOCUMENTS

| | | |
|---|---|---|
| EP | 0 280 784 B1 | 11/1990 |
| EP | 0 543 406 A1 | 5/1993 |

(Continued)

*Primary Examiner* — Huyen Le
(74) *Attorney, Agent, or Firm* — Karl V Sidor

(57) ABSTRACT

A medical liquid applicator system that includes an applicator grip assembly, a flexible reservoir and an applicator head. The applicator grip assembly is composed of a first section with a first distal end and a second section with a second distal end, a longitudinal axis, a front side, a back side, a predetermined grip length, a predetermined grip width, a fold axis separating the first section and the second section, the fold axis being perpendicular to the longitudinal axis, and a fold-activated dispensing slit located on the fold axis. The flexible reservoir is joined to a back side of the applicator grip assembly and is in liquid communication with the fold-activated dispensing slit. The applicator head is joined to the front side of the applicator grip assembly at the fold axis and is in liquid communication with the dispensing slit. The applicator grip assembly is folded at the fold axis to bring the back side of at least a portion of the first distal end of the first section and the back side of at least a portion of the second distal end of the second section together to define a grip handle having the predetermined grip length and the predetermined grip width. Folding the applicator grip assembly ruptures the fold-activated dispensing slit thereby defining a dispensing opening and also applies pressure to the flexible reservoir element in liquid communication with the dispensing slit to urge flowable medical liquid through the dispensing opening and into the applicator head.

13 Claims, 13 Drawing Sheets

U.S. PATENT DOCUMENTS

| | | | |
|---|---|---|---|
| 4,790,429 A | 12/1988 | Fukushima | |
| 4,812,067 A | 3/1989 | Brown et al. | |
| 4,903,842 A | 2/1990 | Tokuda et al. | |
| RE34,087 E | 10/1992 | Redmond | |
| 5,284,703 A | 2/1994 | Everhart et al. | |
| 5,316,400 A | 5/1994 | Hoyt et al. | |
| 5,320,217 A | 6/1994 | Lenarz | |
| 5,348,191 A | 9/1994 | Dekeyser | |
| 5,427,845 A | 6/1995 | Sawyer et al. | |
| 5,746,352 A | 5/1998 | Corella | |
| 6,041,930 A | 3/2000 | Cockburn | |
| 6,288,134 B1 | 9/2001 | Leenslag | |
| 6,315,480 B1 | 11/2001 | Martel et al. | |
| 6,433,034 B1 | 8/2002 | Leenslag et al. | |
| 6,536,974 B2 | 3/2003 | Redmond | |
| 6,595,940 B1 | 7/2003 | D'Alessio et al. | |
| 6,765,035 B2 | 7/2004 | Eling et al. | |
| 6,878,320 B1 | 4/2005 | Alderson et al. | |
| 6,902,335 B2 | 6/2005 | Bergey et al. | |
| 6,945,391 B2 | 9/2005 | Moodie | |
| 6,997,355 B2 | 2/2006 | Duquet et al. | |
| 7,004,322 B1 | 2/2006 | Bartoli | |
| 7,121,409 B1 | 10/2006 | Hamilton et al. | |
| 7,350,677 B2 | 4/2008 | Duquet et al. | |
| 7,506,762 B2 * | 3/2009 | Nelson et al. | 206/484.1 |
| 2003/0173235 A1 | 9/2003 | Balkenhol et al. | |
| 2004/0016771 A1 | 1/2004 | Redmond | |
| 2004/0253039 A1 | 12/2004 | Stenton | |
| 2005/0047846 A1 | 3/2005 | Narang et al. | |
| 2006/0283727 A1 | 12/2006 | Nelson et al. | |

FOREIGN PATENT DOCUMENTS

| | | |
|---|---|---|
| EP | 1 227 047 A1 | 7/2002 |
| WO | WO 97/06073 A1 | 2/1997 |
| WO | WO 99/25530 A1 | 5/1999 |
| WO | WO 01/17875 A1 | 3/2001 |
| WO | WO 01/44071 A1 | 6/2001 |
| WO | WO 02/40353 A1 | 5/2002 |
| WO | WO 2006/041446 A1 | 4/2006 |

* cited by examiner

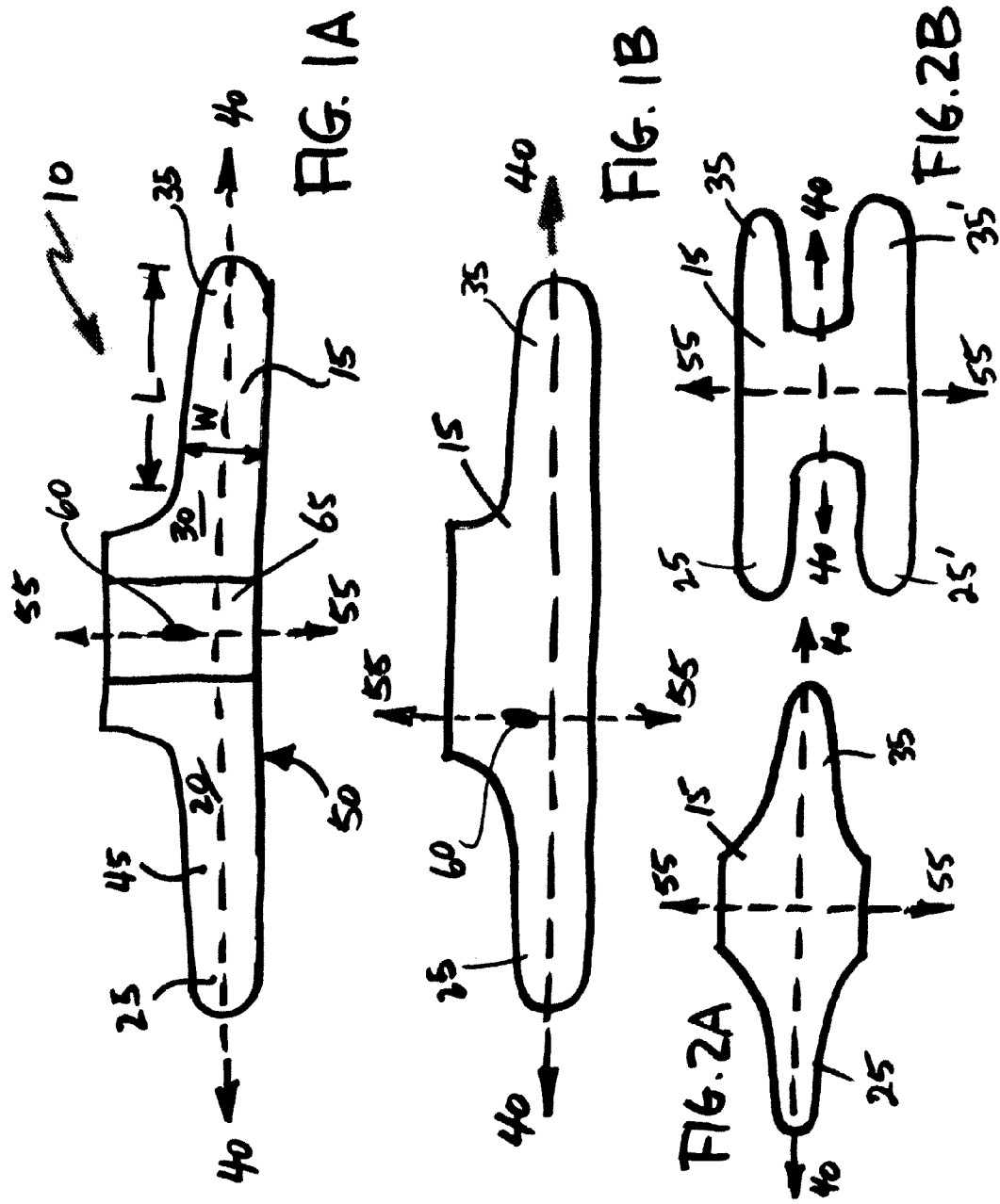

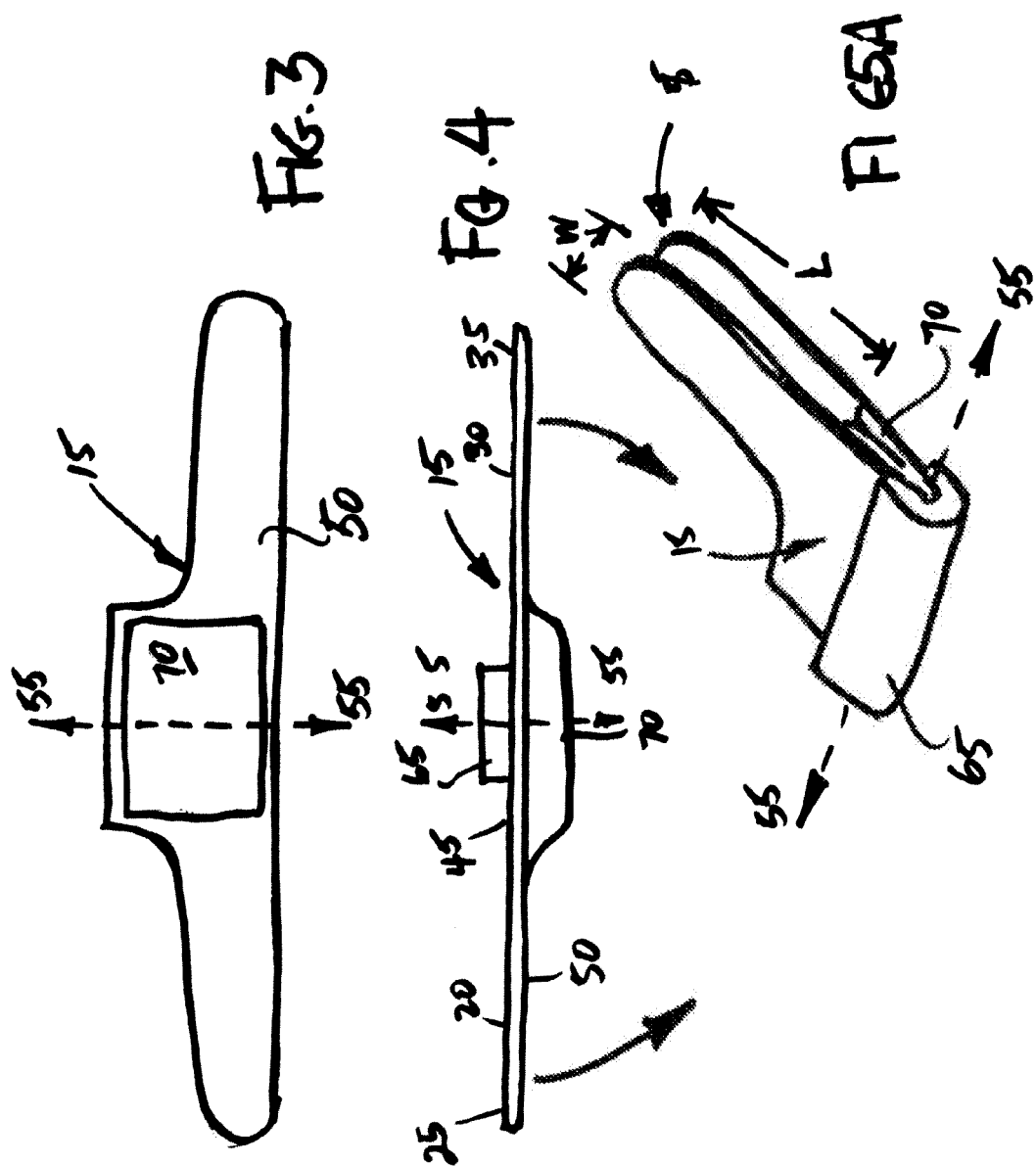

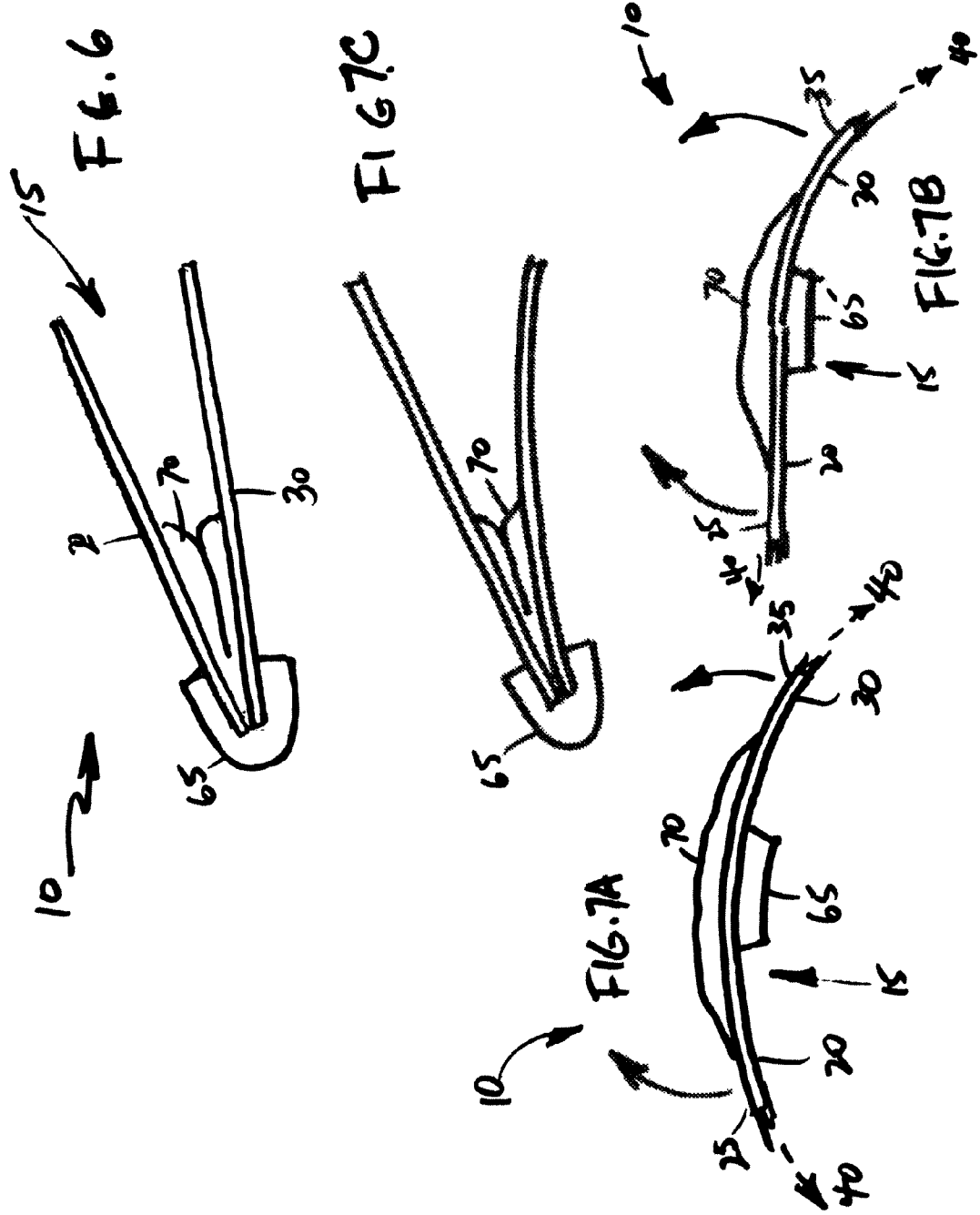

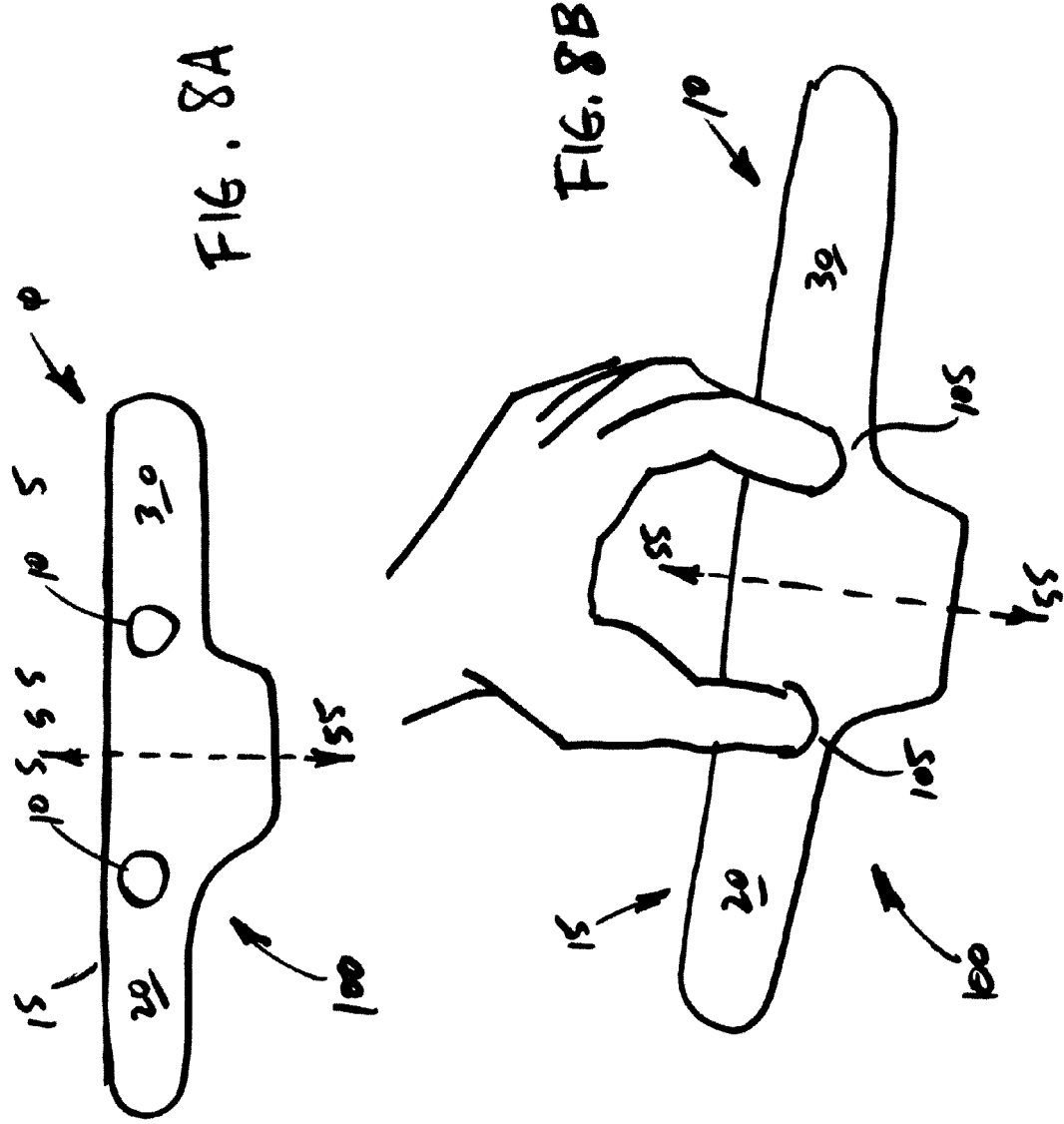

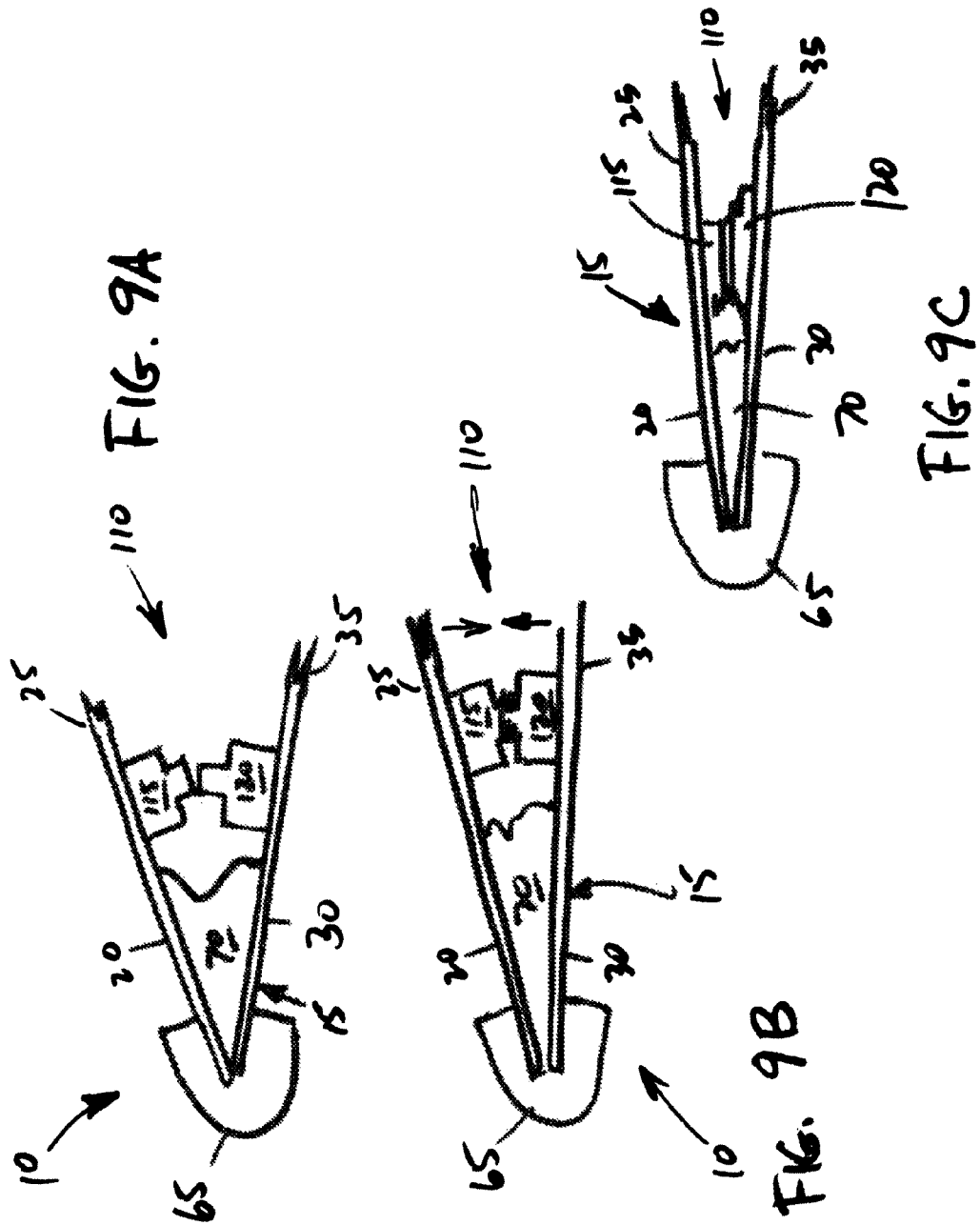

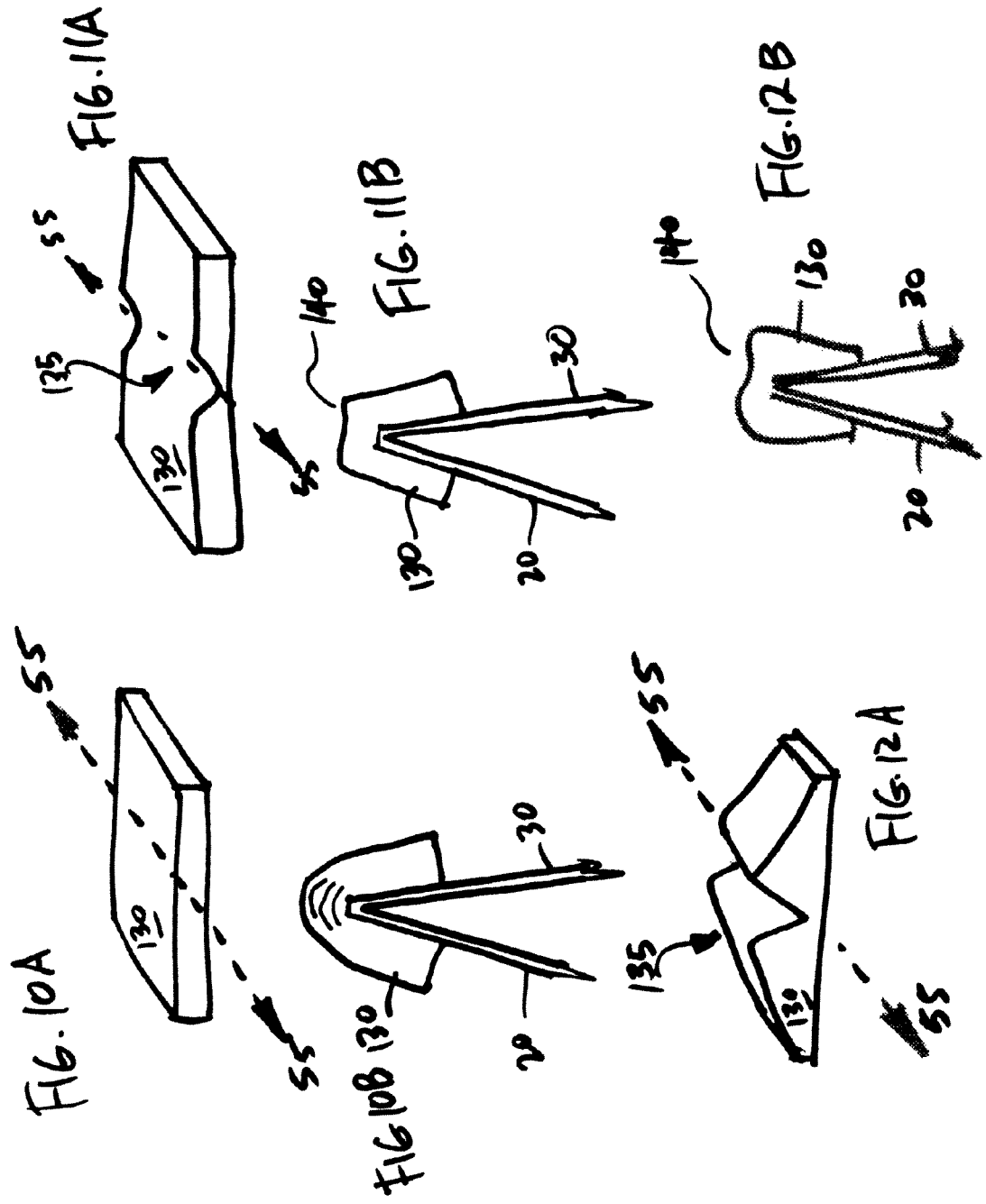

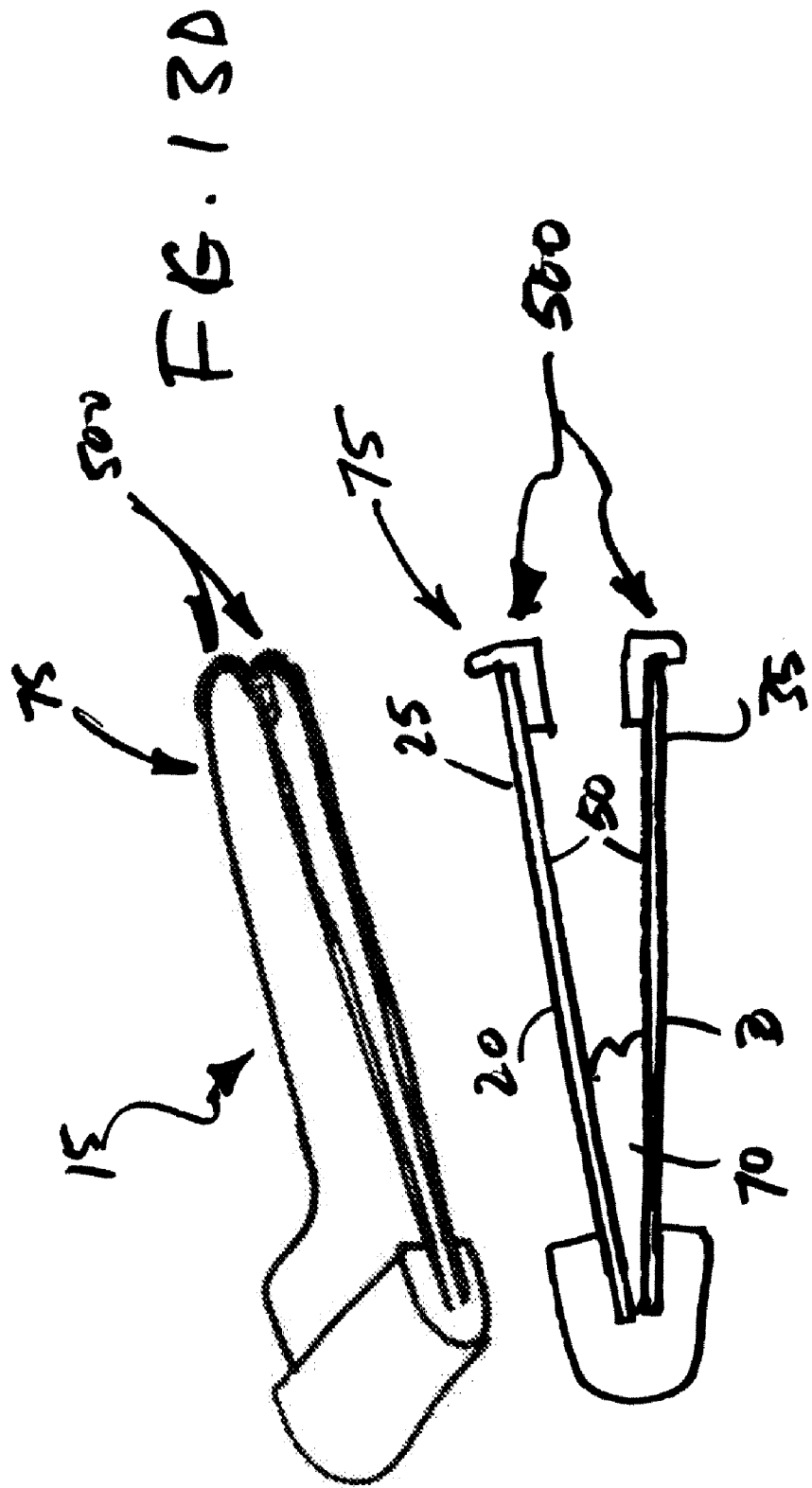

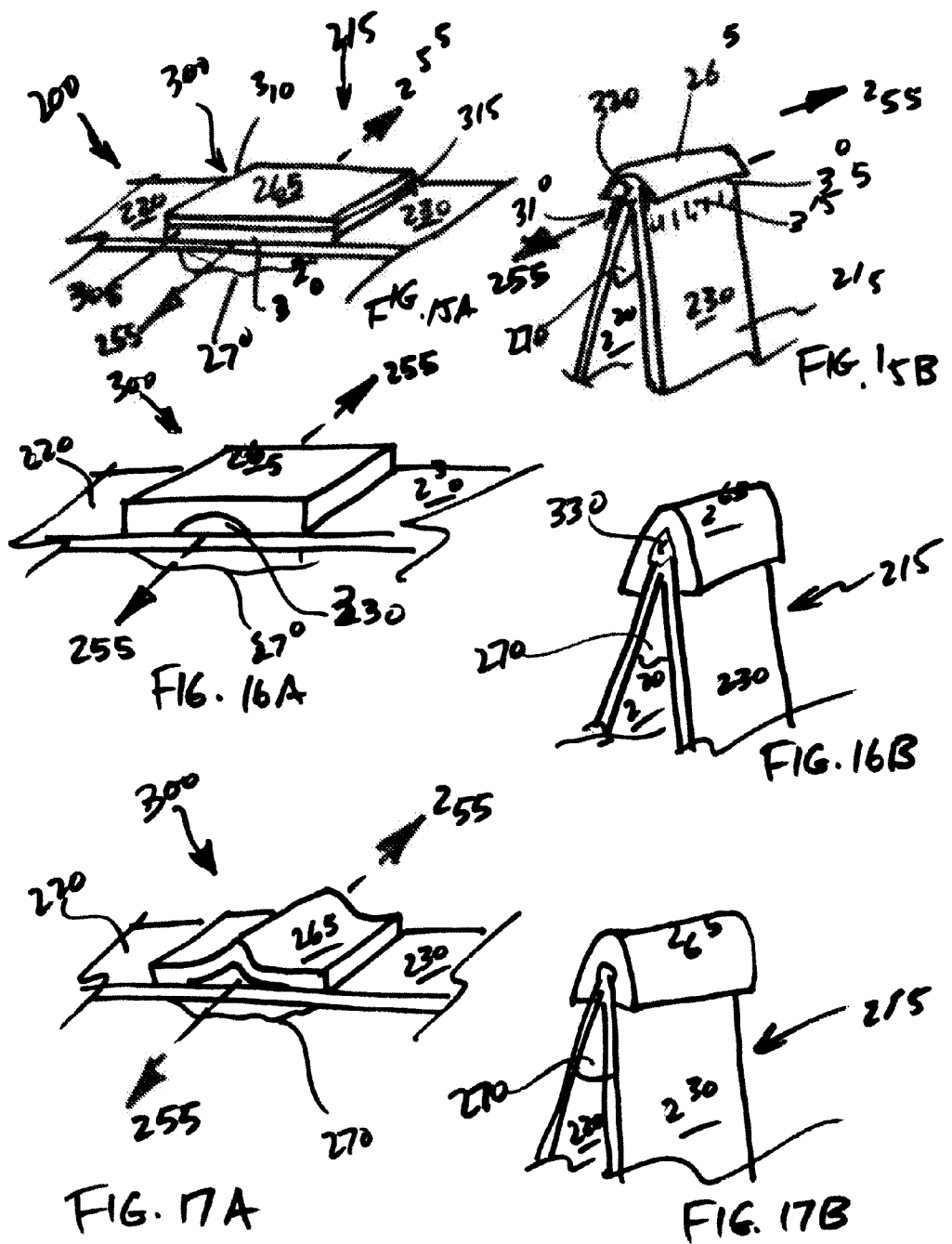

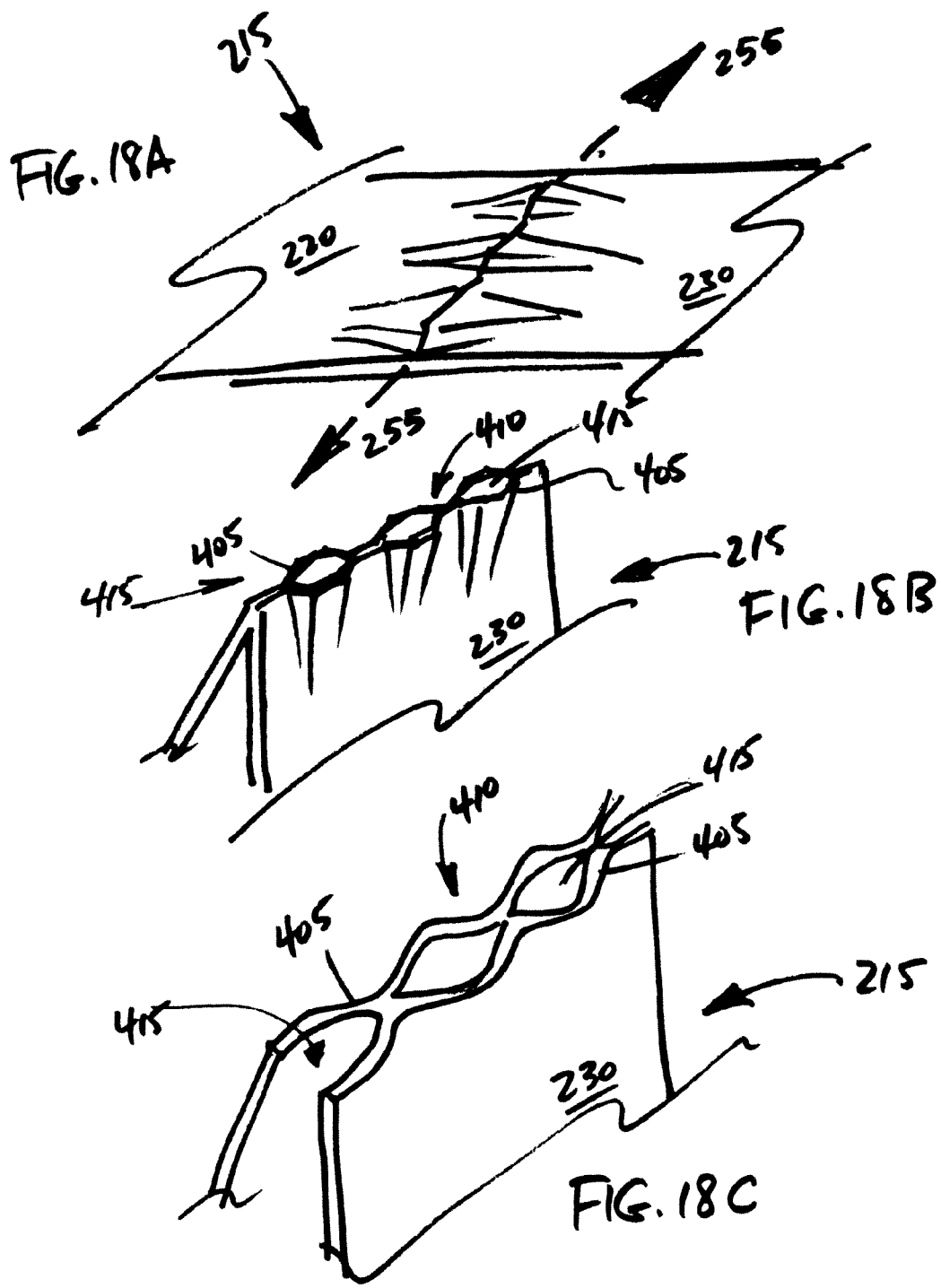

MEDICAL LIQUID APPLICATOR SYSTEM

FIELD OF THE INVENTION

The present invention relates in general to an applicator for applying medical liquids.

BACKGROUND OF THE INVENTION

Folding swabs, folding cards and other types of folding disposable applicators for dispensing liquids are known. Examples of these applicators may be found in U.S. Pat. No. 3,369,267 to Friedland, et al.; U.S. Pat. No. 4,084,910 to LaRosa; U.S. Pat. No. 4,140,409 to DeVries; U.S. Pat. No. 4,430,013 to Kaufman; U.S. Pat. No. 4,493,574 to Redmond, et al.; U.S. Pat. No. 5,316,400 to Hoyt, et al.; U.S. Pat. No. 7,121,409 to Hamilton, et al.; U.S. Patent Application Publication No. US 2005/0047846 to Narang, et al.; and U.S. Patent Application Publication No. US 2006/0283727 to Nelson, et al.

These disposable applicators provide advantages in dispensing and are generally considered to be economical for dispensing small quantities of liquids such as, for example, hand sanitizer and then discarded after a single use. However, these applicators have not gained acceptance for dispensing and applying relatively larger volumes of medical liquids, particularly surgical prep solutions. One problem with these disposable applicators is they are designed for dispensing small quantities of liquids. Typical amounts of liquid are less than 0.5 milliliters. These current conventional designs are configured to be grasped between two or three fingers. Some of the current conventional designs also disclose a swab, felt or foam applicator tip to aid in application of the dispensed liquid.

While some of the current, conventional designs indicate they can be provided in various sizes, scaling up these designs to handle relatively larger volumes of liquids such as, for example, surgical prep solutions would be unsatisfactory. For example, finger griping would become problematic with a larger article both because of the awkwardness of holding the larger applicator with the fingers and the increased weight of the larger quantity of liquid. These large volumes of liquids may gush or over-saturate an applicator head causing waste or difficulty in accurately dispensing and applying a uniform quantity of liquid. Larger foam or swab applicator heads can become distorted and compressed during the folding typically needed to activate the dispenser. Distorted or compressed applicator heads may reduce the amount of liquid dispensing, reduce the control over the rate and uniformity of liquid dispensing and have a negative impact on liquid distribution. A larger card will also make it more difficult to fold the article to activate and initiate dispensing with one hand.

Accordingly, there is an unmet need for a medical liquid applicator system that holds relatively larger quantities of liquids, including but not limited to surgical prep solutions, than conventional disposable folding card-type applicators and yet is so inexpensive that it can be discarded after only a single use. There is also an unmet need for a medical liquid applicator system that holds relatively larger quantities of liquids than conventional disposable folding card-type applicators that is also easy to activate with one hand and that is also able to accurately and conveniently dispense liquids. Moreover, there is an unmet need for an applicator head assembly for use with such a medical liquid applicator system that enhances fluid flow and provides more uniform distribution of liquid.

BRIEF SUMMARY OF THE INVENTION

The problems described above are addressed by the present invention which encompasses a medical liquid applicator system.

The medical liquid applicator system is a single-use, disposable, hand-held system, that includes an applicator grip assembly, a flexible reservoir and an applicator head.

The applicator grip assembly is a substantially rigid, flat, planar applicator grip assembly composed of a first section with a first distal end and a second section with a second distal end, a longitudinal axis, a front side, a back side, a predetermined grip length, a predetermined grip width, a fold axis separating the first section and the second section, the fold axis being perpendicular to the longitudinal axis, and a fold-activated dispensing slit located on the fold axis. The fold axis may be equidistant from the first distal end and second distal end of the applicator grip assembly. Alternatively, the fold axis may be asymmetrically placed between the first distal end and the second distal end of the applicator grip assembly. At least one section of the applicator grip assembly may include a grip enhancer and/or a feature to enhance folding of the applicator grip assembly with one hand.

The flexible reservoir is joined to a back side of the applicator grip assembly. The reservoir may be a flexible pouch and should hold at least 1 milliliter (more desirably, from 1 to 30 milliliters) of a flowable medical liquid such as, for example, a surgical prep solution. The flexible reservoir is in liquid communication with the fold-activated dispensing slit.

The applicator head is joined to the front side of the applicator grip assembly at the fold axis and is in liquid communication with the dispensing slit. The applicator head is desirably made of a porous material adapted to receive the flowable medical liquid and to release the flowable medical liquid to a substrate.

The applicator head may be a porous, liquid permeable cellular material. In an aspect of the invention, the applicator head may have a generally non-planar cross-sectional profile at the fold axis prior when the applicator grip assembly is in unfolded and a generally planar cross-section profile at the fold axis when the applicator grip assembly is folded. In yet another aspect of the invention, the geometry of the applicator head may allow the porous, liquid permeable cellular material of the applicator head to change position while avoiding substantial changes in the density of the porous, liquid permeable cellular material upon folding of the planar grip assembly at the fold axis.

According to the present invention, the applicator grip assembly is folded at the fold axis to bring the back side of at least a portion of the first distal end of the first section and the back side of at least a portion of the second distal end of the second section together to define a grip handle having the predetermined grip length and the predetermined grip width. Folding the applicator grip assembly will rupture the fold-activated dispensing slit thereby defining a dispensing opening and also apply pressure to the flexible reservoir element in liquid communication with the dispensing slit to urge flowable medical liquid through the dispensing opening and into the applicator head.

The applicator grip assembly is formed of substantially rigid material selected from plastic, cardboard, reinforced paper, metal and combinations thereof. At least one section of the applicator grip assembly may have a concave cross-section along the longitudinal axis. The predetermined grip length of the applicator grip assembly may be from about 7 cm to about 20 cm and the predetermined grip width may be from about 2 cm to about 10 cm.

At least a portion of the flexible reservoir overlaps the fold axis. The flexible reservoir desirably contains from at least about 1 milliliter to about 30 milliliters of the flowable medical liquid.

In an aspect of the invention, at least one section of the applicator grip assembly may have at least one pressure resistance stopper along the longitudinal axis to resist the complete contact between the back side of the first distal end of the first section and the back side of the second distal end of the second section.

In another aspect of the invention, the medical liquid applicator system may include a liquid distribution component which may be positioned between the flexible reservoir and the applicator head. For example, the liquid distribution component may be a nonwoven material positioned between the flexible reservoir and the applicator head. Alternatively and/or additionally, the medical liquid applicator system may further include a fastening system to engage the first distal end and the second distal end as they are brought together to define a grip handle. The fastening system may be a mechanical and/or adhesive fastening system.

According to the present invention, the applicator system may further include:
- a spacer section intermediate the first section and the second section of the applicator grip assembly;
- a first fold axis between the first section and the spacer section and a second fold axis between the second section and the spacer section, each fold axis being perpendicular to the longitudinal axis, the spacer section having a length much shorter than the first section and the second section; and
- at least one fold-activated dispensing slit located on at least one fold axis.

With this configuration, the applicator grip assembly folds at each fold axis to define a grip handle. Folding the applicator grip assembly will rupture the at least one fold-activated dispensing slit thereby defining at least one dispensing opening and will also apply pressure to the flexible reservoir element in liquid communication with the dispensing slit to urge flowable medical liquid through the dispensing opening and into the applicator head.

The present invention also encompasses an applicator head assembly for a single-use, disposable, hand-held folding liquid dispenser. The applicator head assembly includes: 1) A porous applicator head positioned across at least one fold axis joining a first section and a second section of an applicator grip assembly; and 2) a liquid distribution component in communication with the porous applicator head and a liquid reservoir in the applicator grip assembly.

The applicator grip assembly is the type that in which the first section and the second section are folded at the fold axis to initiate dispensing of liquid from a liquid reservoir. The liquid distribution component is located between the applicator grip assembly and the porous applicator head and is positioned across the fold axis joining the first section and the second section of the applicator grip assembly or at least one fold axis if there are multiple fold axes. According to the invention, folding the applicator grip assembly generates or alters the liquid distribution component.

In one embodiment of the invention, folding the applicator grip assembly at the fold axis may expose at least an edge of the first section or the second section of the applicator grip assembly having a corrugated configuration to define a liquid distribution channel between the applicator assembly and the porous applicator head. In another embodiment of the invention, folding the applicator grip assembly at the fold axis may cause at least an edge of the first section or the second section of the applicator grip assembly to collapse or separate a collapsible or frangible material to define a liquid distribution channel between the applicator assembly and the porous applicator head. In yet another embodiment of the invention, folding the applicator grip assembly at the fold axis may cause a separator attached to a back side of at least one of the first section or the second section of the applicator grip assembly to separate the first section and the second section of the applicator grip assembly to define a liquid distribution channel between the applicator assembly and the porous applicator head.

In an aspect of the invention, the applicator head may have a generally non-planar cross-sectional profile at the fold axis prior when the applicator grip assembly is unfolded and a generally planar cross-section profile at the fold axis when the applicator grip assembly is folded.

In yet another aspect of the invention, the geometry of the applicator head may allow the porous, liquid permeable cellular material of the applicator head to change position while avoiding substantial changes in the density of the porous, liquid permeable cellular material upon folding of the planar grip assembly at the fold axis.

These and other features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the Invention with reference to the accompanying drawing figures, in which like reference numerals denote similar structure and refer to like elements throughout, and in which:

FIG. 1A is a top view illustration of an exemplary medical liquid applicator system and FIG. 1B is a top view illustration highlighting a feature of an exemplary medical liquid applicator system;

FIGS. 2A and 2B are top view illustrations highlighting features of exemplary medical liquid applicator systems;

FIG. 3 is a bottom view illustration of an exemplary medical liquid applicator system;

FIG. 4 is a cross-sectional view illustration of an exemplary medical liquid applicator system;

FIG. 5A is a perspective view illustration showing an exemplary folded medical liquid applicator system;

FIG. 6 is a cross-sectional view illustration of an exemplary medical liquid applicator system;

FIGS. 7A, 7B and 7C are cross-sectional view illustrations highlighting features of exemplary medical liquid applicator systems;

FIG. 8A is a top view illustration highlighting a feature of an exemplary medical liquid applicator system;

FIG. 8B is a perspective view illustration highlighting a feature of an exemplary medical liquid applicator system FIGS. 9A, 9B and 9C, are cross-sectional view illustrations highlighting features of exemplary medical liquid applicator systems;

FIG. 10A is a perspective view illustration highlighting a feature of an exemplary medical liquid applicator system;

FIG. 10B is a cross-sectional view illustration highlighting a feature of an exemplary medical liquid applicator system;

FIG. 11A is a perspective view illustration highlighting a feature of an exemplary medical liquid applicator system;

FIG. 11B is a cross-sectional view illustration highlighting a feature of an exemplary medical liquid applicator system;

FIG. 12A is a perspective view illustration highlighting a feature of an exemplary medical liquid applicator system;

FIG. 12B is a cross-sectional view illustration highlighting a feature of an exemplary medical liquid applicator system;

FIG. 13C is a cross-sectional view illustration highlighting a feature of an exemplary medical liquid applicator system;

FIGS. 15A and 15B are perspective view illustrations highlighting a feature of an exemplary medical liquid applicator system;

FIGS. 16A and 16B are perspective view illustrations highlighting a feature of an exemplary medical liquid applicator system;

FIGS. 17A and 17B are perspective view illustrations highlighting a feature of an exemplary medical liquid applicator system;

FIGS. 18A, 18B and 18C are perspective view illustrations highlighting a feature of an exemplary medical liquid applicator system;

DEFINITIONS

Figure 5B:
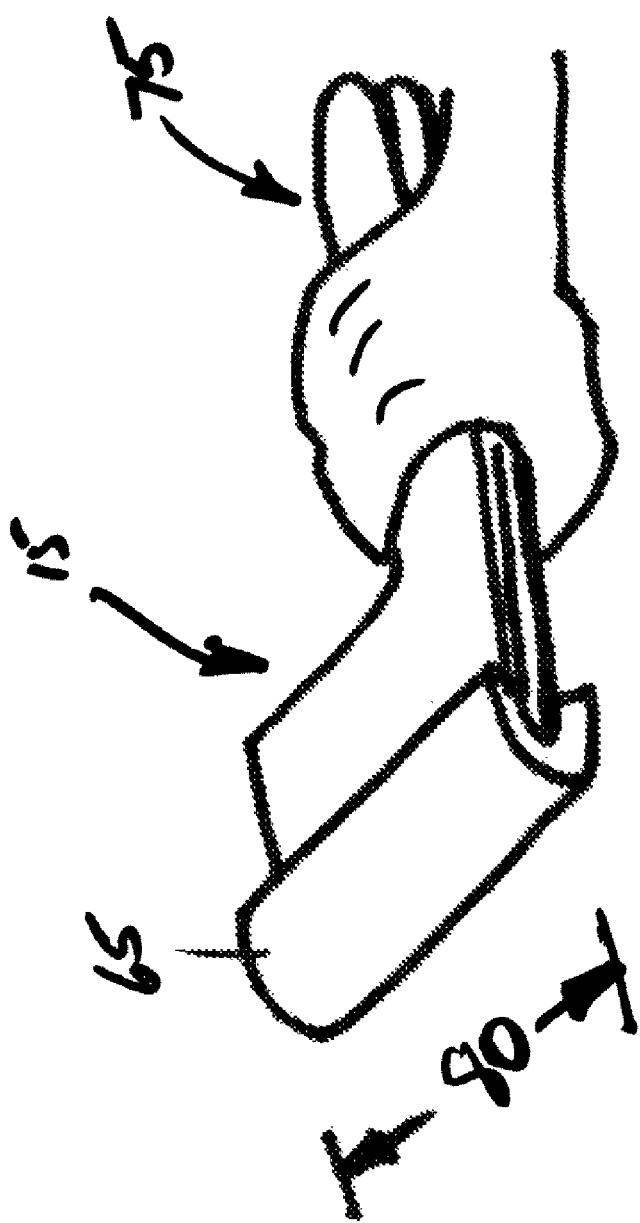
FIG. 5B is a perspective view illustration showing an exemplary folded medical liquid applicator system grasped in the hand of a user.

The term "auxetic foam" refers to a foam structure that exhibits a negative Poisson's ratio. Specifically, an "auxetic foam" is a material or assembly of materials that expands in one or more directions when placed under tension. Thus, auxetic foam can become fatter in one or more directions when stretched. Exemplary auxetic foam materials are disclosed at, for example, U.S. Pat. No. 6,878,320; U.S. Pat. No. 6,765,035; U.S. Pat. No. 6,433,034; and U.S. Pat. No. 6,288,134. An auxetic foam or similar auxetic material may be made of either a material that, due to its inherent structure has a negative Poisson's Ratio or a material that does not inherently have a negative Poisson's Ratio but has been further processed (e.g., combined with an auxetic material, bonded with a pattern causing the processed material to have auxetic behavior, formed into an auxetic macro structure, and the like) so as to be provided with such a negative ratio.

The term "disposable" refers to a product that is so inexpensive that it may economically be discarded after only a single use. Products that are "disposable" are typically intended for single use or may be intended for limited use.

The term "limited use" refers to a product which is intended to be discarded after a few usage events, such events amounting to a few uses for the same person over a period of time (i.e., not limited to single use but also refers to products that are relatively inexpensive to the consumer so the product can economically be discarded if it becomes soiled, needs laundering or otherwise needs to be restored after the few usage events).

The term "longitudinal" refers to a direction running from a first distal end to an opposite distal end of an unfolded applicator grip assembly and generally parallel to the maximum linear dimension of the article. Directions within 25 degrees of the longitudinal direction are considered to be "longitudinal".

The term "medical liquid" refers to liquids, foams, gels and combinations thereof that are applied to a surface or substrate such as, for example, the skin of a mammal to prepare, treat, clean, sanitize that surface or substrate. One non-limiting example of a medical liquid is a surgical site preparation liquid, foam or gel. Another non-limiting example of a medical liquid is a skin sealant that is applied to the skin prior to surgery or after surgery.

The term "Poisson's Ratio" refers to the ratio of an orthogonal strain in response to a strain resulting from a stretching force or a compressive force.

The term "single-use" refers to a product that is intended to be used for only once and is not intended to be re-used, re-conditioned, restored or repaired after that use.

DETAILED DESCRIPTION OF INVENTION

In describing the various embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Thus, exemplary embodiments of the invention are presented herein; however, the invention may be embodied in a variety of alternative forms, as will be apparent to those skilled in the art. To facilitate understanding of the invention, and provide a basis for the claims, various figures are included in the description.

The figures are not drawn to scale and related elements may be omitted so as to emphasize the novel features of the invention. Structural and functional details depicted in the figures are provided for the purpose of teaching the practice of the invention to those skilled in the art and are not intended to be considered limitations. Directional terms such as left, right, front or rear are provided to assist in the understanding of the invention and are not intended to be considered as limitations.

Referring now to FIG. 1A, there is shown an illustration of a top plan view of one embodiment of an exemplary medical liquid applicator system 10. The medical liquid applicator system 10 includes an applicator grip assembly 15 that is substantially rigid, flat, and planar prior to folding. The applicator grip assembly 15 is composed of a first section 20 with a first distal end 25 and a second section 30 with a second distal end 35, a longitudinal axis 40, a front side 45, a back side 50, a predetermined grip length "L", a predetermined grip width "W", a fold axis 55 separating the first section 20 and the second section 30, the fold axis 55 being perpendicular to the longitudinal axis 40, and a fold-activated dispensing slit 60 located on the fold axis 55. An applicator head 65 overlapping the fold axis 55 is visible in the top view of the applicator grip assembly.

The fold axis 55 may be equidistant from the first distal end 25 and second distal end 35 of the applicator grip assembly 15 as shown in FIG. 1A. Alternatively and as shown by an illustration of a top view of an exemplary applicator grip assembly in FIG. 1B, the fold axis 55 may be asymmetrically placed between the first distal end 25 and the second distal end 35 of the applicator grip assembly 15. At least one section of the applicator grip assembly may include a grip enhancer located along at least portions of the grip length and grip width. The grip enhancer may be a roughened surface, knobs or bumps a tacky resin, stripes of material or tacky resin, or the like.

Referring now to FIG. 2A, there is shown an illustration of a top view of an exemplary applicator grip assembly 15 showing a configuration that is more symmetric about the longitudinal axis 40. In this exemplary configuration, the fold axis 55 is shown as equidistant from the first distal end 25 and second distal end 35 of the applicator grip assembly 15 and the distal ends may be brought together by folding at the fold axis 55 to create a grip handle. FIG. 2B is an illustration of a top view of an exemplary applicator grip assembly 15 showing a configuration that is also symmetric about the longitudinal axis 40. In this exemplary configuration, the fold axis 55 is shown as equidistant from the first distal ends 25 and 25' and second distal ends 35 and 35' of the applicator grip assembly 15 and the distal ends may be brought together by folding at the fold axis 55 to create multiple grip handles.

FIG. 3 is an illustration of a bottom view of an exemplary applicator grip assembly 15 showing a flexible reservoir 70 joined to a back side 50 of the applicator grip assembly 15 and overlapping the fold axis 55. The reservoir 70 may be a flexible pouch and should contain at least 1 milliliter of a flowable medical liquid such as, for example, a surgical prep solution. The flexible reservoir 70 is in liquid communication with the fold-activated dispensing slit located on the fold axis 55. Referring now to FIG. 4, there is shown an illustration of a cross-sectional view of an exemplary applicator grip assembly 15 in its unfolded condition. The applicator head 65 is joined to the front side 45 of the applicator grip assembly 15 at the fold axis 55 and is in liquid communication with the dispensing slit. The applicator head 65 is desirably made of a porous material adapted to receive the flowable medical liquid and to release the flowable medical liquid to a substrate. The applicator head 65 may be a porous, liquid permeable cellular material such as, for example, a porous sponge material, a porous foam material, porous open celled foam and/or a liquid permeable auxetic material such as a porous auxetic foam.

The applicator grip assembly 15 is folded at the fold axis 55 in the direction generally depicted by the arrows in FIG. 4 to bring the back side 50 of at least a portion of the first distal end 25 of the first section 20 and the back side 50 of at least a portion of the second distal end 35 of the second section 30 together. These distal ends define a single grip handle 75 having the predetermined grip length "L" and the predetermined grip width "W" as generally illustrated by FIG. 5A in the perspective view of an exemplary folded applicator grip assembly 15. FIG. 5B is a perspective view showing an exemplary folded applicator grip assembly 15 of an medical liquid applicator system as it is grasped in the hand of a user. The predetermined grip length of the applicator grip assembly may be from about 7 cm to about 20 cm and the predetermined grip width may be from about 2 cm to about 10 cm. For example, the predetermined grip length of the applicator grip assembly may be from about 8 cm to about 18 cm and the predetermined grip width may be from about 3 cm to about 8 cm. In an embodiment of the invention, the predetermined grip length of the applicator grip assembly may be from about 9 cm to about 16 cm and the predetermined grip width may be from about 4 cm to about 6 cm. The overall length of the medical liquid applicator system may desirably be in the range of from about 15 to about 35 cm—including the predetermined grip length of the grip handle. For example, the overall length of the medical liquid applicator system may be from about 20 to about 30 cm.

As can be seen from FIG. 5B, the width 80 of portion of the folded applicator grip assembly to which the reservoir 70 is joined is greater than the predetermined grip width "W". The greater width is useful for the relatively larger flexible reservoirs needed to hold larger volumes of medical liquids such as, for example, surgical prep solutions in position such that at least a portion of the flexible reservoir 70 overlaps the fold axis 55. The width 80 may range from about 3 cm to about 15 cm. Desirably, the width 80 may range from about 5 cm to about 11 cm. The predetermined grip width "W" of the grip handle will desirably be less than the width 80 of the applicator grip assembly. The flexible reservoir 70 desirably contains from at least about 1 milliliter to about 30 milliliters of the flowable medical liquid. More desirably, the flexible reservoir 70 desirably contains from at least about 2 milliliter to about 20 milliliters of the flowable medical liquid. In certain embodiments of the invention, the flexible reservoir 70 contains from at least about 3 milliliter to about 15 milliliters of the flowable medical liquid such as, for example, surgical prep solution. Because of the larger volumes of liquids employed, a larger portion of the flexible reservoir 70 may be located away from the fold axis 55 with only a small or relatively narrower portion of the flexible reservoir forming a channel that overlaps the fold axis and dispensing slit. Such a configuration permits the applicator grip assembly to be folded and the handles brought relatively close together without applying excessive amounts of pressure to the flexible reservoir during an initial phase of dispensing liquid.

Examples of surgical prep solutions that may be contained in the flexible reservoir include, but are not limited to, povidone-iodine based formulations such as, for example BETADINE® Solution (aqueous solution of 10% povidone-iodine), a commonly used surgical preparation liquid and is available from Purdue Products, L.P. of Stamford, Conn. Other examples include chlorhexidine gluconate based formulations such as, for example, ChloraPrep® patient preoperative skin preparation solution available from Cardinal Health, Inc. of Dublin, Ohio.

Of course, other medical liquids, gels, foams, skin sealants and/or adhesives may be used with the medical liquid applicator system. An important aspect of the medical liquid applicator system is that it provides satisfactory dispensing of relatively large volumes of liquid while desirably keeping healthcare workers' hands away from the skin or surface receiving the liquid. According to the invention, the grip handle of the medical liquid applicator system will keep the hands of a user at least about 6 to about 10 cm or more away from the skin or surface receiving the liquid. This distance is typically a vertical distance. Desirably, the grip handle of the medical liquid applicator system will keep the hands of a user at least about 7 or 8 to about 10 cm away from the skin or surface receiving the liquid. Another aspect is that the invention provides a grip handle so a healthcare worker can adequately hold the applicator containing heavier weights of liquid (from the larger volumes) and quickly apply and manipulate the applicator. In this respect, the combination of the grip handle, flexible reservoir and applicator head serves as a type of "paintbrush" or wand that is easily manipulated and well-suited for applying a liquid to a surface. Another aspect of the invention is that the larger volume of liquid requires improved liquid distribution to adequately saturate a larger applicator head as well as improved metering to avoid over-saturating the applicator head during activation (i.e., folding) and initial application of liquid.

Figure 5C:
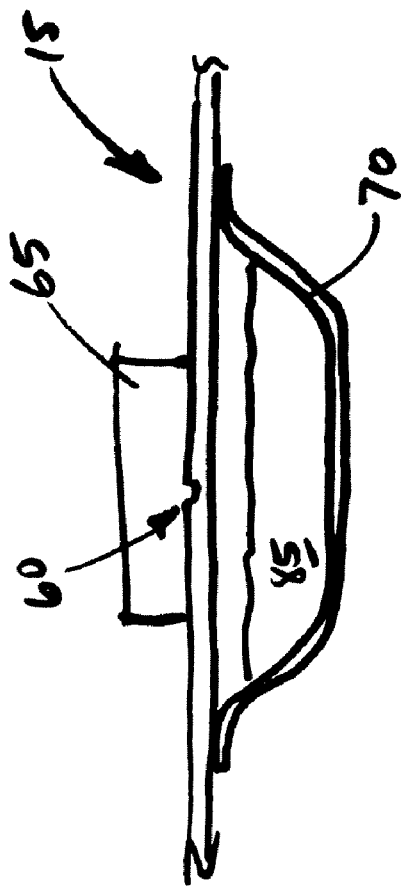
FIGS. 5C, 5D and 5E, are cross-sectional view illustrations of an exemplary medical liquid applicator system.
Figure 5E:
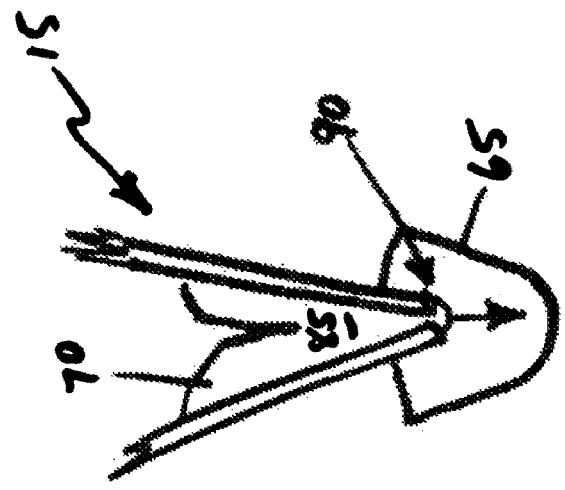
Figure 5D:
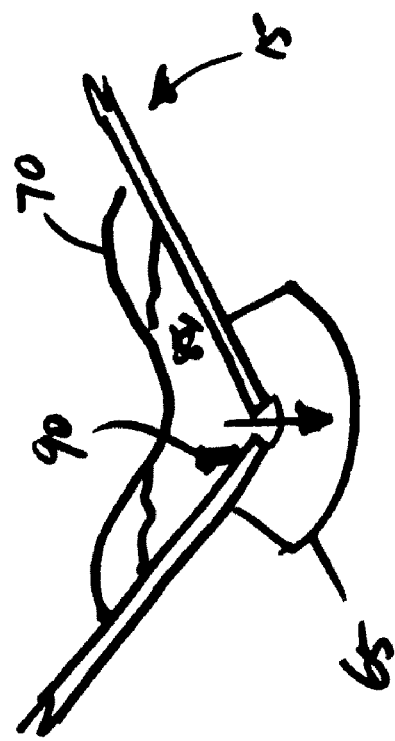

FIGS. 5C, 5D and 5E are illustrations showing cross-sectional views of the applicator grip assembly 15 prior to and during folding. As seen from these illustrations, folding the applicator grip assembly 15 will rupture or otherwise open the fold-activated dispensing slit 60 thereby defining a dispensing opening 95. Folding the applicator grip assembly 15 will also apply pressure to the flexible reservoir 70 in liquid communication with the dispensing slit 60 to urge flowable medical liquid 85 through the dispensing opening 95 and into the applicator head 65.

The applicator grip assembly is formed of substantially rigid material selected from plastic, cardboard, reinforced paper, metal and combinations thereof. A variety of materials may be used and the rigidity of the material should be sufficient to provide for reliable folding and dispensing. That is, because of the volume (and weight) of the flowable liquid and the size of the applicator grip assembly, the material should be sufficiently rigid to apply pressure to urge or force the liquid from the flexible reservoir and into the applicator head without being too flexible. If material of the applicator grip assembly is too flexible, it will be difficult to generate the appropriate pressure for satisfactory dispensing. The applicator grip assembly may contain reinforcing ribs or other features to stiffen the article. The portion of the applicator grip assembly surrounding the fold axis 55 may desirably lack some or all of any optional reinforcing features to reduce the force needed to fold the grip assembly.

In an aspect of the invention, at least one of the first and/or second sections of the applicator grip assembly may have a concave cross-section along the longitudinal axis. That is, one of the sections of the applicator grip assembly may be curved in the dimension running from the fold axis 55 to a distal end of a section to amplify the effect of bringing the distal ends together and to compensate for at least some flexibility that may be present in the material used to form the applicator grip assembly. Referring to FIG. 6, there is shown an illustration of a cross-section of an exemplary medical liquid applicator system 10 in a folded condition in which the first section 20 and the second section 30 of the grip assembly 15 each have a generally flat, planar cross sectional configuration.

FIG. 7A is an illustration of a cross-section of an exemplary medical liquid applicator system 10 in which the grip assembly 15 has a generally concave cross-section along the entire longitudinal axis 40 when the grip assembly is in an unfolded condition. That is, the first section 20 and the second section 30 of the grip assembly 15 separated by the fold axis 55 may each have a generally concave cross-sectional configuration. During use, the first distal end 25 and the second distal end 35 is folded together in the directions of the arrows in the drawing. FIG. 7B is an illustration of a cross-section of an exemplary medical liquid applicator system 10 in which the grip assembly 15 has a generally concave cross-section along only a portion of the longitudinal axis 40 when the grip assembly is in an unfolded condition. That is, the first section 20 of the grip assembly has a generally flat cross-section and the second section 30 of the grip assembly 15 separated by the fold axis 55 has a generally concave cross-section. During use, the first distal end 25 and the second distal end 35 is folded together in the directions of the arrows in the drawing. Of course, the mirror-image configuration is contemplated. That is, the first section 20 of the grip assembly may have a generally concave cross-section and the second section 30 of the grip assembly 15 may have a generally flat cross-section. FIG. 7C is an illustration of a cross-section of an exemplary medical liquid applicator system 10 in which the first section 20 of the grip assembly has a generally flat cross-section and the second section 30 of the grip assembly 15 separated by the fold axis 55 has a generally concave cross-section while in a folded condition. When such a concave configuration is utilized, it is contemplated that the material in at least portions of the applicator assembly may have slightly greater flexibility than materials used to construct the applicator grip assembly when no concave configuration is employed.

FIG. 8A is an illustration of a top view of an embodiment of an exemplary medical liquid applicator system 10 that includes a fold assist feature 100 which enables one handed folding of the applicator grip assembly 15. The fold assist feature 100 may be one or more openings 105 defined by the applicator grip assembly (e.g., a pair of finger holes) as generally shown in FIG. 8A. For example, a finger opening 105 may be defined in the first section 20 and in the second section 30 of the applicator grip assembly 15. In order to fold the applicator grip assembly 15 to activate the medical liquid applicator system 10, the user inserts a finger in each opening 105 and pinches or squeezes the first section 20 and the second section 30 of the applicator grip assembly 15 together. Desirably, a thumb and index finger may be used as generally illustrated in FIG. 8B but other configurations for other combinations of fingers are contemplated. Finger openings are only one embodiment of the fold assist feature 100. Other configurations are contemplated including, but not limited to, loops of material, fabric or thread attached to and/or extending from each section of the applicator grip assembly; notches or grooves formed in and/or made a part of the applicator grip assembly; pouches or pockets formed in and/or joined to the applicator grip assembly; and the like. Combinations of these configurations may be used.

In an aspect of the invention, at least one section of the applicator grip assembly may have at least one pressure resistance stopper along the longitudinal axis to provide increasing resistance to the complete contact between the back side of the first distal end of the first section and the back side of the second distal end of the second section. The pressure resistance stopper may be a collapsible element formed in the applicator grip assembly or attached to the applicator grip assembly. Generally speaking, the resistance can be set so that the user expels a predetermined amount of medical liquid from the reservoir upon activation to saturate the applicator. After that initial amount of liquid is dispensed, additional pressure is needed to be applied by the user to overcome the resistance provided by the pressure resistance stopper such as collapsing a bubble or shell molded in the applicator grip assembly, folding a bending an element or squeezing a collapsible foam such as, for example, the foam used in collapsible foam earplugs.

Referring now to FIG. 9A to 9C, there is shown a series of illustrations of a cross-section of an exemplary medical liquid applicator system 10 incorporating a pressure resistance stopper 110 in the form of a first stopper 115 attached to a distal end 25 of the first section 20 and a second stopper 120 attached to the distal end 35 of the second section 30 of the applicator grip assembly 15. As can be seen in FIG. 9A, the first stopper 115 contacts the second stopper 120 to provide resistance. The dimensions and locations of the stoppers 115 and 120 are configured to provide resistance to the pressure applied to the flexible reservoir 70 from a user squeezing the grip handle after an initial amount of liquid is dispensed. As more pressure is applied to bring the first section 20 and the second section 30 closer together to dispense more liquid from the flexible reservoir 70, one or both of the first stopper 115 and the second stopper 120 yield(s) to permit additional liquid to be dispensed from the flexible reservoir as generally illustrated in FIG. 9B. Each stopper (or only one stopper) may be designed to have a single collapse pressure or single stage or single resistance level or it can be designed to have multiple collapse pressures or multiple stages or multiple resistance levels. Multiple stoppers may be arranged in series along a longitudinal axis of the applicator grip assembly or a single stopper may be at one location on the applicator grip assembly. The stopper(s) may be joined on one or both sections of the applicator grip assembly. As additional pressure is applied, one or both of the first stopper 115 and the second stopper 120 yield(s) again to permit even more liquid to be dispensed from the flexible reservoir as generally illustrated in FIG. 9C.

Referring now to FIG. 10A, there is illustrated in cross-section an exemplary porous liquid-permeable applicator head 130 having a uniform and planar cross-section. In a typical use, the applicator head 130 is folded along the fold axis 55 of the applicator grip assembly. Since the applicator head 130 is adhered to the applicator grip assembly on each side of the fold axis 55, folding the applicator head 130 tends to compress the porous liquid-permeable material at the fold axis 55 as generally shown in FIG. 10B. This phenomenon tends to reduce or inhibit the flow of liquid into and through the applicator head 130. This is particularly noticeable as the thickness of the applicator head 130 increases (e.g., as the height of the applicator head increases in the Z dimension). In an aspect of the invention and as generally illustrated in cross-section in FIG. 11A and 12A, the applicator head 130 may have a generally non-planar cross-sectional profile 135 at the fold axis 55 prior when the applicator head attached to the applicator grip assembly is in an unfolded state and a generally planar cross-section profile 140 at the fold axis 55 when the applicator head attached to the applicator grip assembly is folded as shown by the cross-section illustration in FIG. 11B and FIG. 12B. As can be understood from this description and the illustrations, the geometry of the applicator head may allow the porous, liquid permeable cellular material of the applicator head to change position while avoiding substantial changes in the density of the porous, liquid permeable cellular material upon folding of the planar grip assembly at the fold axis because the portion of the applicator head at the fold axis is relatively thin in comparison to portions of the applicator head adjacent the fold axis 55.

It is also contemplated that the material of the applicator head 130 may allow the porous, liquid permeable cellular material of the applicator head to change position while avoiding substantial changes in the density of the porous, liquid permeable cellular material upon folding of the planar grip assembly at the fold axis. For example, the applicator head may be made of or may include auxetic materials such as auxetic foams. Such foams may be produced by heating standard open cell foam (e.g., polyurethane foam) and compressing it in all three dimensions while at an elevated temperature. The foam is then cooled while under compression. Without being bound by theory, it is believed that such processing transforms the foam into one where the ribs/walls defining the foam cells are buckled inwardly forming a re-entrant cell structure. Longitudinal expansion of such re-entrant foams results in lateral expansion (i.e., such foams are an auxetic material). Auxetic materials of this type are described in U.S. Pat. No. 4,668,557 "Polyhedron Cell Structure and Method of Making Same" and a scaled up process for making such materials is described in PCT publication WO1999025530 A1 "Scale-Up of Negative Poisson's Ratio Foams".

Figure 13A:
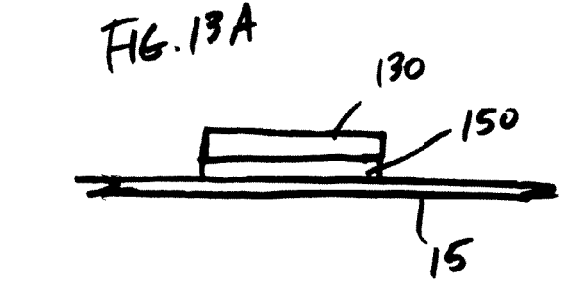
FIGS. 13A and 13B are cross-sectional view illustrations highlighting a feature of an exemplary medical liquid applicator system.
Figure 13B:

Referring now to FIG. 13A, a liquid distribution layer 150 may be positioned between the applicator grip assembly 15 and the applicator head 130 so the liquid from the flexible reservoir may be more uniformly present on the applicator head 130. For example, the liquid distribution layer positioned between the applicator grip assembly 15 and the applicator head 130 may be a nonwoven liquid distribution material. Exemplary nonwoven liquid distribution materials may be low basis weight spundbond polyolefin materials available from Kimberly-Clark Corporation or hydraulically entangled nonwoven or composite nonwoven structures available from Kimberly-Clark Corporation. Examples include materials described in U.S. Pat. No. 5,284,703 and U.S. Pat. No. 5,427,845. These materials may have a very low density and a relatively low level of bonding so that the liquid distribution layer 150 may bend readily and desirably deform when the applicator grip assembly is folded so that the applicator head 130 remains porous and uncompressed as generally illustrated in FIG. 13B.

FIG. 13C is an illustration showing a cross-section of an aspect of the medical liquid applicator system highlighting a fastening system 500 located at the back side 50 of the first distal end 25 of the first section 20 and the back side 50 of the second distal end 35 of the second section 30. The fastening system 500 is configured to engage the first distal end 25 and the second distal end 35 as they are brought together to define a grip handle 75 as generally illustrated in FIG. 13D by a perspective view of the applicator grip assembly 15. The fastening system 500 may be a mechanical fastening system. Exemplary mechanical fastening systems include, but are not limited to, hook and loop fastening systems (e.g., mechanical fastening systems available under the Velcro® brand); snap fasteners; interlocking fasteners such as male-female elements molded or embossed into the distal ends; magnetic fasteners; loops of plastic, fabric or other materials; rubberbands or other elastic fasteners; or combinations of the same. These fastening systems 500 may be configured to extend beyond the planar surface of the first distal end 25 and/or the second distal end 35 to provide a grip stop, grip knob or other similar feature that helps to prevent a hand gripping the grip handle from slipping past the distal end of the grip handle.

Figure 14A:
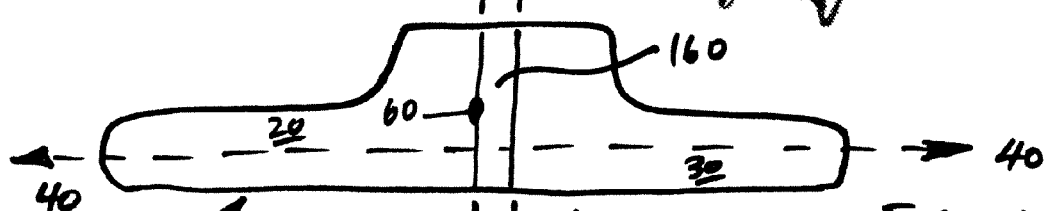
FIG. 14A is a top view illustration highlighting a feature of an exemplary medical liquid applicator system.
Figure 14B:
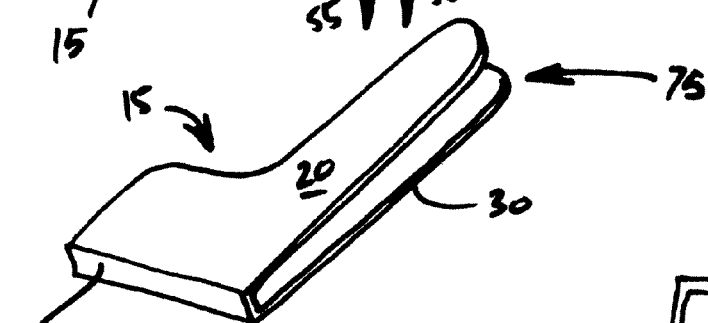
FIG. 14B is a perspective view illustration highlighting a feature of an exemplary medical liquid applicator system.
Figure 14C:
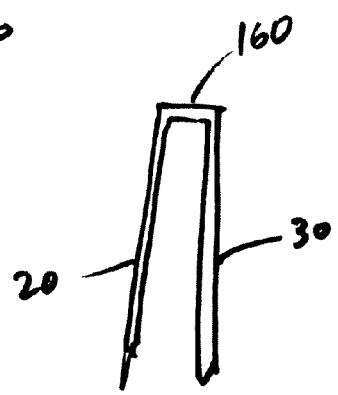
FIG. 14C is a cross-section view illustration highlighting a feature of an exemplary medical liquid applicator system.

Referring now to FIGS. 14A through 14C, the medical liquid applicator system may further include a spacer section 160 to increase the useful surface area of the applicator head 130. FIG. 14A is a top view of an applicator grip assembly 15 showing the spacer section 160. FIG. 14B is a perspective view of the applicator grip assembly 15 showing the spacer section 160. FIG. 14C is a cross-section view of the applicator grip assembly 15 showing the spacer section 160. The spacer section 160 is intermediate the first section 20 and the second section 30 of the applicator grip assembly 15. That is, a first fold axis 55 is located between the first section 20 and the spacer section 160 and a second fold axis 55' is located between the second section 30 and the spacer section 160. Each fold axis 55 and 55' being perpendicular to the longitudinal axis 40. As can be seen in the FIGS. 14A through 14C, the spacer section 160 has a length (as measured along the longitudinal axis 40 of the applicator grip assembly 15) that is much shorter than the length of the first section 20 and/or the second section 30 (as measured along the longitudinal axis 40 of the applicator grip assembly 15). According to the invention at least one fold-activated dispensing slit 60 is located on at least one of the fold axes. With this configuration, the applicator grip assembly 15 folds at each fold axis 55 and 55' to define a grip handle 75. Folding the applicator grip assembly 15 will rupture the at least one fold-activated dispensing slit thereby defining at least one dispensing opening and will also apply pressure to the flexible reservoir element in liquid communication with the dispensing slit to urge flowable medical liquid through the dispensing opening and into the applicator head.

The present invention also encompasses an applicator head assembly for a single-use, disposable, hand-held folding liquid dispenser. Referring generally to FIGS. 15A, 15B, 16A, 16B, 17A, 17B, 18A, 18B and 18C, the applicator head assembly 200 includes a porous applicator head 265 positioned across at least one fold axis 255 joining a first section 220 and a second section 230 of an applicator grip assembly 215; and a liquid distribution component 300 in communication with the porous applicator head 265 and a liquid reservoir 270 in the applicator grip assembly 215.

The applicator grip assembly 215 is the type that in which the first section 220 and the second section 230 are folded at the fold axis 255 to initiate dispensing of liquid from the flexible liquid reservoir 270. The liquid distribution component 300 is located between the applicator grip assembly 215 and the porous applicator head 265 and is positioned across the fold axis 255 joining the first section 220 and the second section 230 of the applicator grip assembly or at least one fold axis if there are multiple fold axes. According to the invention, folding the applicator grip assembly generates the liquid distribution component 300 or alters the liquid distribution component 300.

As shown in perspective view in FIG. 15A, the liquid distribution component 300 may be a material 305 that is collapsible, stretchable or otherwise frangible and which has a first edge 310, a second edge 315 and an interior 320. The material 305 may be, for example, a very weak porous foam material or a layer of nonwoven material having a low density and a very low level of bonding. The material 305 should have a coherent structure when the applicator grip assembly 215 is in the unfolded condition. The material 305 is adhered or joined to the applicator grip assembly 215 and the porous applicator head 265 and overlaps the fold axis 255. Referring to FIG. 15B, it is illustrated in perspective view that folding the applicator grip assembly at the fold axis 255 desirably causes at least a first edge 310 and/or a second edge 315 of the liquid distribution component 305 to stretch or expand so that the porous applicator head 265 is relatively less deformed as a result of the folding. According to the invention, the material 305 absorbs the forces caused by folding the applicator grip assembly 215 and is deformed or altered so that the porous applicator head 265 can remain relatively intact which helps to preserve the porous, uncompressed nature of the applicator head and provide more satisfactory dispensing than would be expected of the porous applicator head 265 if it were also deformed by folding the applicator grip assembly 215. Alternatively and/or additionally, an edge of the first section 220 or the second section 220 of the applicator grip assembly 215 may to stretch or otherwise expand to separate the material 305 to define a liquid distribution channel 320 between a dispensing opening of the applicator grip assembly 215 and the porous applicator head 265. The liquid distribution channel 320 is generally thought to enhance the distribution of liquid onto the porous applicator head 265.

Referring to the perspective view illustrated in FIG. 16A, another aspect of the applicator head assembly 200 is shown in which the liquid distribution component 300 may be a cavity or channel 330 defined in the porous applicator head 265 at the dispensing slit 260 and generally parallel to the dispensing slit 260. The porous applicator head 265 is adhered or joined to the applicator grip assembly 215 such that the cavity or channel 330 overlaps the fold axis 255. Referring to FIG. 16B, it is illustrated in perspective view that folding the applicator grip assembly at the fold axis 255 desirably causes the porous applicator head to stretch or expand so that the porous applicator head 265 at least partially takes up or fills in the cavity or channel 330 such that the cavity or channel is altered as a result of the folding. According to the invention, the altering of the cavity or channel 330 allows the displacement of the material of the porous applicator head 365 caused by folding the applicator grip assembly 215 with relatively little compression or compaction so that the porous applicator head 265 can remain relatively intact which helps to preserve the porous nature of the applicator head and provide more satisfactory dispensing.

Referring to FIG. 17A, another aspect of the applicator head assembly 200 is illustrated in perspective view in which the liquid distribution component 300 may be a cavity or channel 330 defined by bunching or gathering excess material of the porous applicator head 265 at the dispensing slit located at the fold axis 255 to either compress the material or to create a pleat the extends upward in a direction generally perpendicular to the plane of the dispensing slit and applicator grip assembly 215 in its unfolded state. The porous applicator head 265 is adhered or joined to the applicator grip assembly 215 in a matter that creates a cavity or channel 330 overlapping the fold axis 255. Referring to FIG. 17B, it is illustrated in perspective view that folding the applicator grip assembly at the fold axis 255 desirably causes the excess material of the porous applicator head 265 to move in a manner that at least partially takes up or fills in the cavity or channel 330 such that the cavity or channel is altered as a result of the folding. According to the invention, the displacement of the excess material of the porous applicator head 365 caused by folding the applicator grip assembly 215 results in relatively little compression or compaction of the porous applicator head 265 so it can remain relatively intact which helps to preserve the porous nature of the applicator head and provide more satisfactory dispensing.

Referring generally to FIGS. 18A, 18B and 18C, it is illustrated in perspective view that the applicator grip assembly 215 may be formed with corrugations or embossments 400 at the fold axis 255 such that folding the applicator grip assembly 215 at the fold axis 255 will expose at least an edge 405 of the first section 220 and/or the second section 230 of the applicator grip assembly 215 having a corrugated or embossed configuration 410 thereby defining a liquid distribution channel 415 between the applicator grip assembly 215 and the porous applicator head (not shown) that is attached to the applicator grip assembly 215 directly over the corrugations or embossments.

Figure 19A:
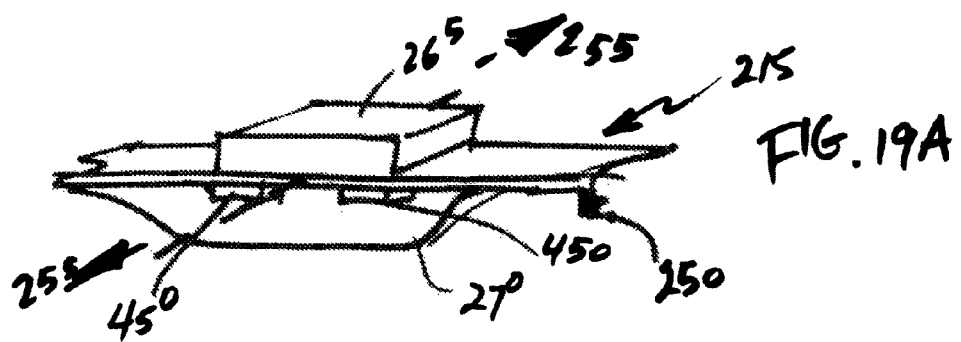
FIGS. 19A, 19B and 19C are perspective view illustrations highlighting a feature of an exemplary medical liquid applicator system.
Figure 19B:
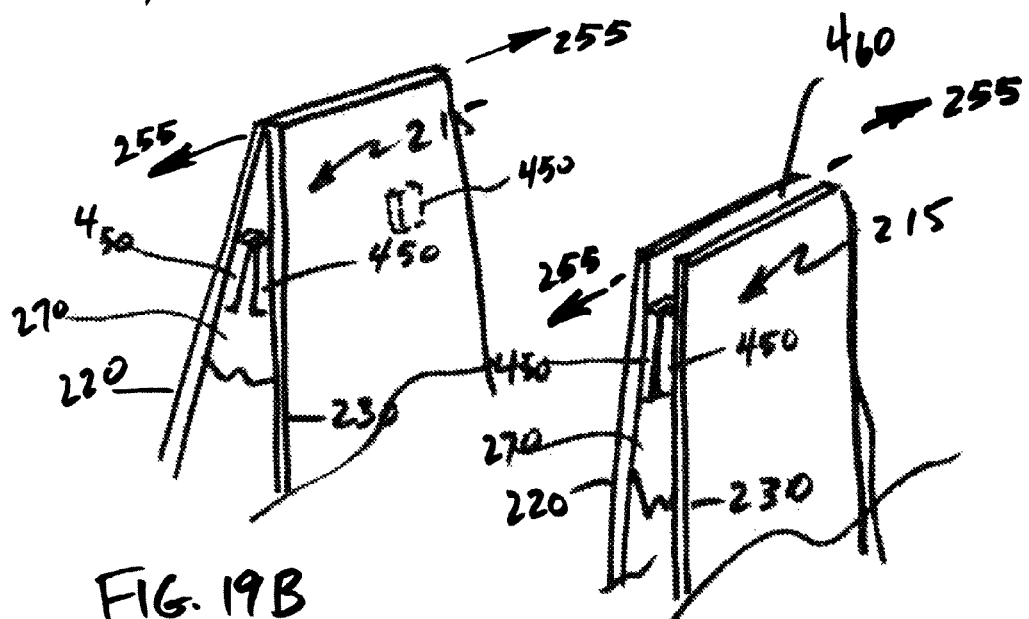
Figure 19C:
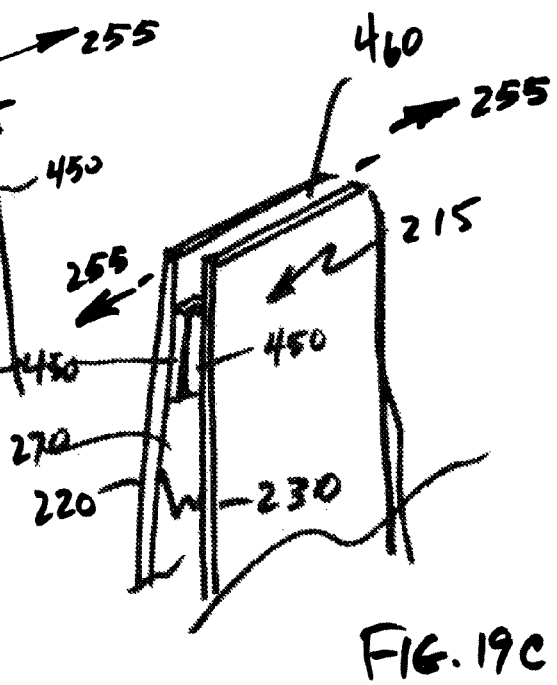

Referring to FIGS. 19A, 19B and 19C, it is illustrated in perspective view that the applicator grip assembly 215 may have at least one separator 450 attached to a back side 250 of the applicator grip assembly on one or both sides of the fold axis 255. The separator(s) 450 may be within the flexible reservoir 270 or, more desirably, they may be positioned very close to the fold axis 255 and out of the way of the flexible reservoir 270. Upon folding of the applicator grip assembly 215 at the fold axis 255, the separator 450 attached to a back side 250 of at least one of the first section 220 or the second section 230 of the applicator grip assembly 215 contact each other. As more pressure is applied to each section of the applicator grip assembly, the sections desirably separate at the fold axis 255 to separate the first section 220 and the second section 230 of the applicator grip assembly to define a liquid distribution channel 460 between the applicator grip assembly 215 and the porous applicator head (not shown). These separators 450 should be discrete and should not be continuous along the backside of the applicator grip assembly in order to facilitate flow of liquid.

In other aspects of the applicator head assembly, the applicator head of the applicator head assembly may have a generally non-planar cross-sectional profile at the fold axis prior when the applicator grip assembly is unfolded and a generally planar cross-section profile at the fold axis when the applicator grip assembly is folded. It is contemplated that the applicator head of the applicator head assembly may have a geometry that permits the porous, liquid permeable cellular material of the applicator head to change position while avoiding substantial changes in the density of the porous, liquid permeable cellular material upon folding of the planar grip assembly at the fold axis.

These and other features and advantages of the invention will become more apparent to one skilled in the art from the following description and claims when read in light of the accompanying drawings.

While particular embodiments of the present invention have been described herein; it will be apparent to those skilled in the art that alterations and modifications may be made to the described embodiments without departing from the scope of the appended claims.

What is claimed is:

1. A single-use, disposable, hand-held medical liquid applicator system, the applicator system comprising:
    a substantially rigid, flat, planar applicator grip assembly comprising a first section having a first distal end and a second section having a second distal end, a longitudinal axis, a front side, a back side, a predetermined grip length, a predetermined grip width, a fold axis separating the first section and the second section, the fold axis being perpendicular to the longitudinal axis, and a fold-activated dispensing slit located on the fold axis;
    a flexible reservoir joined to a back side of the applicator grip assembly, the reservoir comprising a flexible pouch and containing at least 1 milliliter of a flowable medical liquid, and the flexible reservoir in liquid communication with the fold-activated dispensing slit;
    an applicator head joined to the front side of the applicator grip assembly at the fold axis and in liquid communication with the dispensing slit, the applicator head comprising a porous material adapted to receive the flowable medical liquid and to release the flowable medical liquid to a substrate;
    a spacer section intermediate the first section and the second section of the applicator grip assembly;
    a first fold axis between the first section and the spacer section and a second fold axis between the second section and the spacer section, each fold axis being perpendicular to the longitudinal axis, the spacer section having a length much shorter than the first section and the second section; and
    a first fold-activated dispensing slit located on a first fold axis and a second fold-activated dispensing slit located on a second fold axis;
    wherein the applicator grip assembly is adapted to fold at each fold axis to define a grip handle and further to rupture both fold-activated dispensing slits thereby defining multiple dispensing opening and apply pressure to the flexible reservoir element in liquid communication with the dispensing slit thereby urging flowable medical liquid through the dispensing opening and into the applicator head.

2. The applicator system of claim 1, wherein the applicator grip assembly is formed of substantially rigid material selected from plastic, cardboard, reinforced paper, metal and combinations thereof.

3. The applicator system of claim 1, wherein the predetermined grip length is from about 7 cm to about 20 cm and the predetermined grip width is from about 2 cm to about 10 cm.

4. The applicator system of claim 1, wherein at least a portion of the flexible reservoir overlaps the fold axis.

5. The applicator system of claim 1, wherein the flexible reservoir contains from at least about 1 milliliter to about 30 milliliters of the flowable medical liquid.

6. The applicator system of claim 1, wherein the fold axis is equidistant from the first distal end and second distal end of the applicator grip assembly and at least one section of the applicator grip assembly contains a grip enhancer or a fold assist feature.

7. The applicator system of claim 1, wherein at least one section of the applicator grip assembly has a concave cross-section along the longitudinal axis.

8. The applicator system of claim 1, wherein at least one section of the applicator grip assembly has at least one pressure resistance stopper along the longitudinal axis to resist the complete contact between the back side of the first distal end of the first section and the back side of the second distal end of the second section.

9. The applicator system of claim 1, wherein the system further includes a liquid distribution layer positioned between the flexible reservoir and the applicator head.

10. The applicator system of claim 1, wherein the system further includes a fastening system to engage the first distal end and the second distal end as they are brought together to define a grip handle.

11. The applicator system of claim 1, wherein the applicator head is a porous, liquid permeable cellular material.

12. The applicator system of claim 11, wherein the applicator head has a generally non-planar cross-sectional profile at the fold axis prior when the applicator grip assembly is in an unfolded state and a generally planar cross-section profile at the fold axis when the applicator grip assembly is folded.

13. The applicator system of claim 11, wherein the geometry of the applicator head allows the porous, liquid permeable cellular material of the applicator head to change position while avoiding substantial changes in the density of the porous, liquid permeable cellular material upon folding of the planar grip assembly at the fold axis.

* * * * *